(12) United States Patent
Tanaami et al.

(10) Patent No.: US 7,209,236 B2
(45) Date of Patent: Apr. 24, 2007

(54) BIOCHIP READER

(75) Inventors: Takeo Tanaami, Tokyo (JP); Yasunori Suzuki, Tokyo (JP); Yumiko Sugiyama, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 28 days.

(21) Appl. No.: 11/176,287

(22) Filed: Jul. 8, 2005

(65) Prior Publication Data

US 2006/0050275 A1   Mar. 9, 2006

(30) Foreign Application Priority Data

Jul. 9, 2004   (JP)   ............ P. 2004-202547

(51) Int. Cl.
*G01N 21/25* (2006.01)

(52) U.S. Cl. .................................... 356/417; 250/458.1

(58) Field of Classification Search .................. 356/417
See application file for complete search history.

(56) References Cited

U.S. PATENT DOCUMENTS 6,888,630 B2 *   5/2005   Tanaami et al. ............ 356/317

FOREIGN PATENT DOCUMENTS

| JP | 2001-194309 A | 7/2001 |
|---|---|---|
| JP | 2001-194310 A | 7/2001 |
| JP | 2003-28799 A | 1/2003 |
| JP | 2003-57557 A | 2/2003 |
| JP | 2004-138420 A | 5/2004 |

* cited by examiner

*Primary Examiner*—Gregory J. Toatley, Jr.
*Assistant Examiner*—Roy M. Punnoose
(74) *Attorney, Agent, or Firm*—Sughrue Mion, PLLC (57) ABSTRACT

A biochip reader has a microlens plate having a plurality of microlenses, a light source which applies coherent light to the microlens plate as excitation light, a dichroic mirror which transmits or reflects outgoing light from the microlens plate, and reflects or transmits fluorescence occurring on a biochip, a photographing section, a lens which collects the light reflected or transmitted on the dichroic mirror into the photographing section, a barrier filter provided between the dichroic mirror and the photographing section, and a driving section which drives the microlens plate, wherein while the driving section drives the microlens plate, excitation light diverged or collected by the plurality of microlenses scans a surface of the biochip. Each of the microlenses having arbitrary size are provided on the microlens plate at arbitrary positions, An outgoing angle at each microlens of divergence light or collection light is limited to a narrow angle.

12 Claims, 13 Drawing Sheets

LIGHT AMOUNT (ARBITRARY VALUE)

CH101

X POSITION

BIOCHIP READER

CROSS-REFERENCE TO RELATED APPLICATIONS

This application is based upon and claims the benefit of priority from the prior Japanese Patent Applications No. 2004-202547, filed on Jul. 9, 2004, the entire contents of which are incorporated herein by reference.

BACKGROUND OF THE INVENTION

1. Field of the Invention

This invention relates to a biochip reader of a DNA chip, a protein chip, etc., and in particular to a biochip reader that can flexibly deal with performance variations of an optical system and secular changes in an optical system and makes it possible to reduce costs.

2. Description of the Related Art

A biochip has a substrate on which several thousand to several ten thousand types of pieces of already known DNA are placed like an array. Using the nature of binding DNA pieces of the same type if a piece of unknown DNA is allowed to flow into such a DNA chip, already known DNA bound is examined using a biochip reader, thereby determining an unknown DNA sequence, etc.

Figure 17:
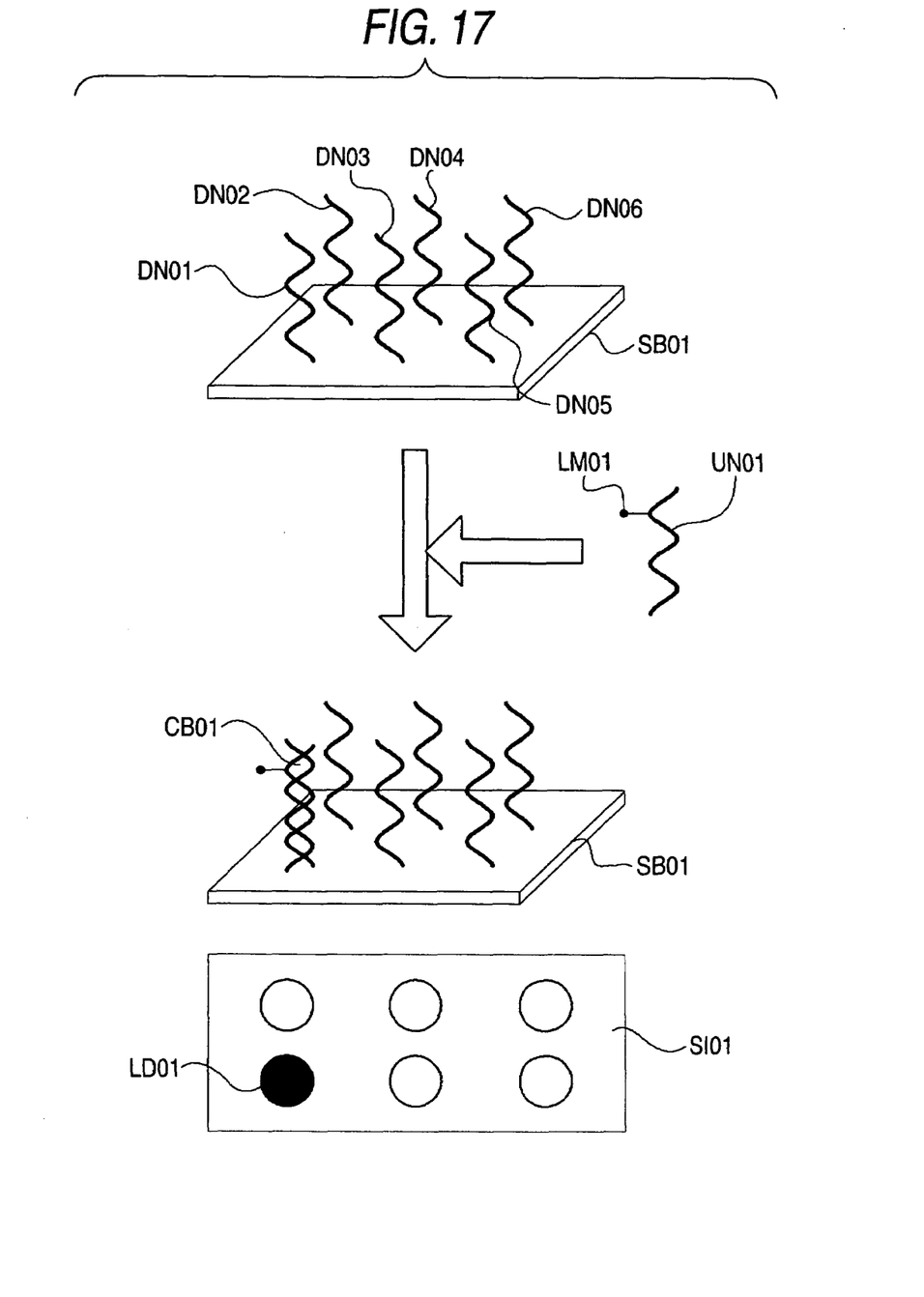
FIG. 17 is a schematic representation to show an example of hybridization on a biochip.

FIG. 17 is a schematic representation to show an example of hybridization on such a biochip. In FIG. 17, sites of six types of DNA pieces indicated by "DN01," "DN02," "DN03," "DN04," "DN05," and "DN06" are placed as an array on a substrate indicated by "SB01", making up a DNA chip.

On the other hand, "UN01" in FIG. 17 is an unknown DNA piece to which a fluorescent mark is previously added as indicated by "LM01" in FIG. 17. Such an unknown DNA piece is hybridized with the above-described DNA chip, whereby the DNA pieces with complementary sequences are bound.

For example, the unknown DNA piece of "UN01" in FIG. 17 is bound with the already known DNA piece of "DN01" in FIG. 17 as "CB01" in FIG. 17.

Using the biochip reader, excitation light is applied to the DNA chip thus hybridized and fluorescence occurring on the fluorescent mark is detected, whereby which piece of already known DNA the unknown DNA piece is bound with can be determined.

For example, fluorescence occurs only in the portion where "CB01" occurs in FIG. 17 in the image of the scanning result of the DNA chip as indicated by "SI01" in FIG. 17 and therefore fluorescence is detected only from the portion indicated by "LD01" in FIG. 17.

JP-A-2001-194309, JP-A-2001-194310, JP-A-2003-028799, JP-A-2003-057557 and JP-A-2004-138420 are referred to as related art relevant to a biochip reader such as a DNA chip or a protein chip.

Figure 18:
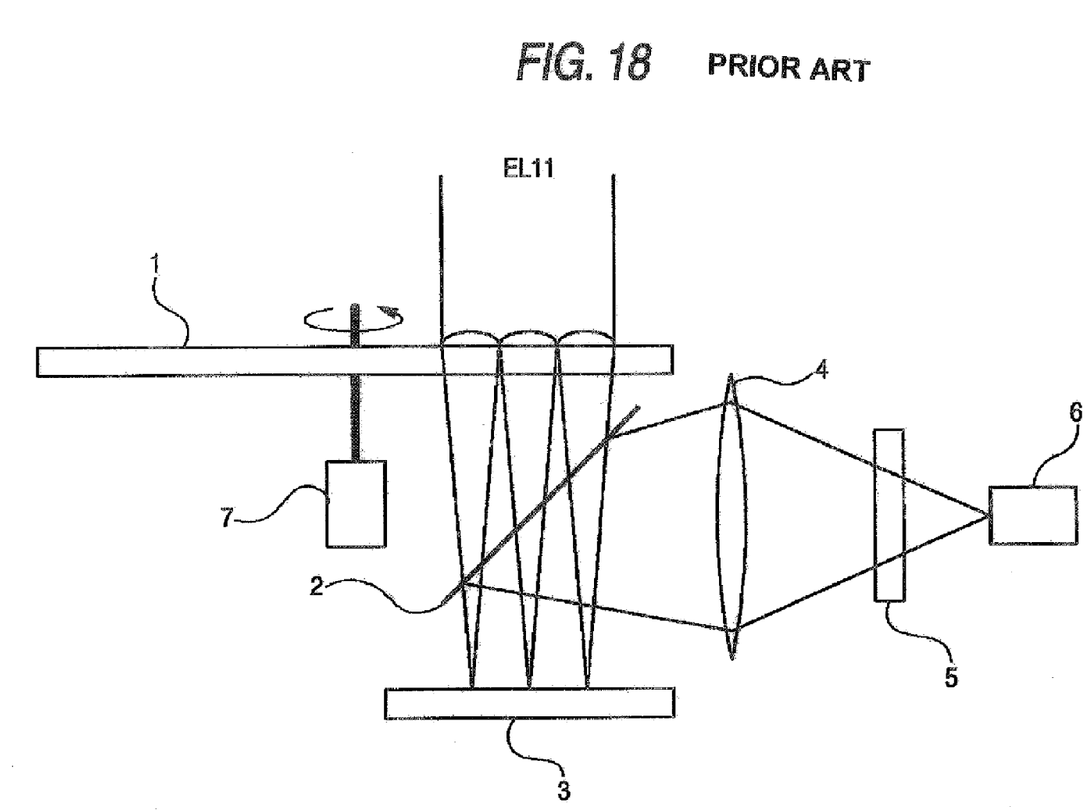
FIG. 18 is a block diagram to show a configuration example of a biochip reader in a related art.

FIG. 18 is a block diagram to show a configuration example of a biochip reader in a related art. In FIG. 18, numeral 1 denotes a microlens plate formed with a plurality of microlenses on a circular substrate, numeral 2 denotes a dichroic mirror for transmitting or reflecting light in response to the wavelength of the light, numeral 3 denotes a biochip having a plurality of sites placed like an array, numeral 4 denotes a lens, numeral 5 denotes a barrier filter for blocking transmission of light in a specific wavelength region, numeral 6 denotes a photographing section such as a camera, and numeral 7 denotes a driving section such as a motor for rotating the microlens plate 1.

Excitation light indicated by "EL11" in FIG. 18, outgoing light from a light source (not shown) such as a laser light source for emitting coherent light, is applied to the microlens plate 1, and the excitation light collected on the microlenses formed on the microlens plate 1 is passed through the dichroic mirror 2 and is collected on the biochip 3.

Fluorescence occurring on the biochip 3 by the excitation light (specifically, fluorescence occurring on the site where a plurality of DNA pieces of the same type are placed) is reflected on the dichroic mirror 2 and the reflected light is passed through the barrier filter 5 by the lens 4 and is collected on the photographing (image capturing) section 6.

On the other hand, the driving section 7 rotates the microlens plate 1 on the center axis of a disk, whereby the positions of the microlenses formed on the microlens plate 1 move and accordingly the excitation light collected on the microlenses scans over the surface of the biochip 3.

Figure 19:
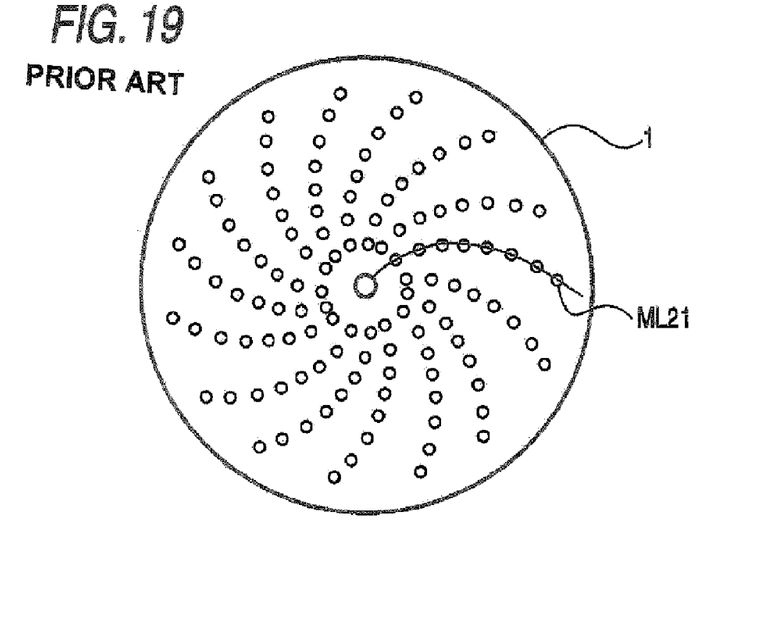
FIG. 19 is a plan view to show an example of a microlens plate.

For example, FIG. 19 is a plan view to show an example of the microlens plate 1. As shown in FIG. 19, the microlenses are arranged spirally as indicated by "ML21" in FIG. 19 on the microlens plate 1 and the microlens plate 1 thus formed with the microlenses is rotated on the center axis, whereby the excitation light collected on the microlenses scans over the surface of the biochip 3. (A pattern example is described in Japanese Patent Nos. 2663766 and 2692416.)

However, in the related art example shown in FIG. 18, the microlenses are formed at the accurate positions of the microlens plate 1 and the center axis is provided accurately and eccentricity of the motor of the driving section 7, rotation synchronization with the camera of the photographing section 6, etc., is required, thus resulting in an increase in cost; this is a problem.

Figure 20:
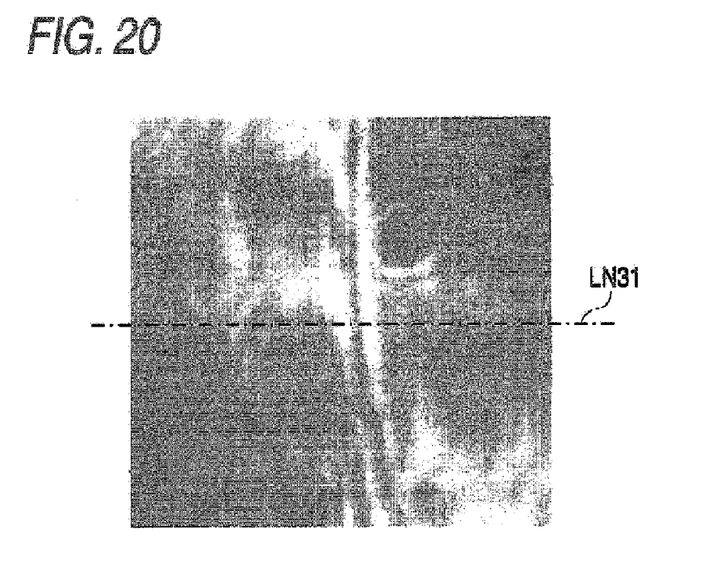
FIG. 20 is a schematic representation to show an example of a photograph image when a fluorescent plate for uniformly producing fluorescence in response to excitation light is used instead of a biochip.
Figure 21:
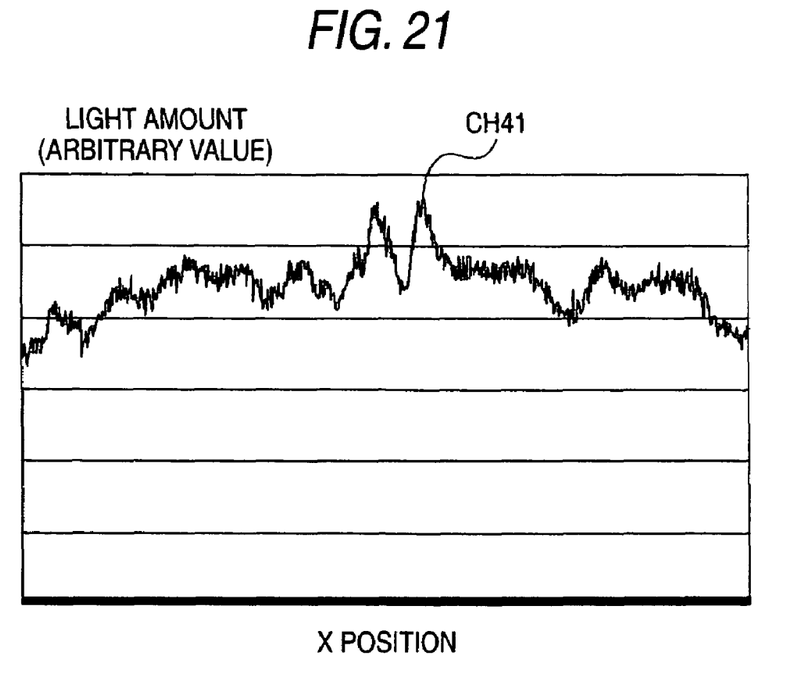
FIG. 21 is a schematic representation to show an example of the distribution characteristic of any axial light amounts when a fluorescent plate for uniformly producing fluorescence in response to excitation light is used instead of a biochip.

To use outgoing light of a laser light source as excitation light, performance variations such as light distribution unevenness of the outgoing light of the laser light source or dirt and secular changes (aging) in the optical system of the lens, the dichroic mirror, etc., directly affect the image photographed with the photographing section 6, worsening S/N; this is a problem For example, FIGS. 20 and 21 are schematic representations to show examples of a photograph image and the distribution characteristic of any axial light amounts when a fluorescent plate for uniformly producing fluorescence in response to excitation light is used instead of the biochip 3.

As shown in FIG. 20, patterns like unevenness and interference fringes caused by performance variations such as light distribution unevenness of the outgoing light of the laser light source or dirt and secular changes in the optical system are reflected on the photograph image although it should be an image with uniform light amount, and it is easily seen that the characteristic curve of light amounts is not uniform light amount and S/N worsens in "CH41" in FIG. 21 indicating the light quantity distribution on the line indicated by "LN31" in FIG. 20.

The reason is that interference noise such as speckle noise easily occurs because coherent light of a laser, etc., is used as the light source.

SUMMARY OF THE INVENTION

An object of the invention is to provide a biochip reader that can flexibly deal with performance variations of an optical system and secular changes in an optical system and makes it possible to reduce costs.

The invention provides a biochip reader including: a microlens plate on which a plurality of microlenses, whose outgoing angle of divergence light or collection light is limited to a narrow angle, are provided at arbitrary positions, wherein each of the plurality of the microlenses has arbitrary size; a light source which applies coherent light to the microlens plate as excitation light; a dichroic mirror which transmits or reflects outgoing light from the microlens plate, and reflects or transmits fluorescence occurring on a biochip; a photographing section; a lens which collects the light reflected or transmitted on the dichroic mirror into the photographing section; a barrier filter provided between the dichroic mirror and the photographing section; and a driving section which drives the microlens plate, wherein while the driving section drives the microlens plate, excitation light diverged or collected by the plurality of microlenses scans a surface of the biochip. Therefore, performance variations of the optical system and secular changes in the optical system can be flexibly dealt with, and it is made possible to reduce the cost of the biochip reader.

In the biochip reader, the plurality of microlenses are formed by providing projections (convex) and depressions (concave) on a substrate of the microlens plate. Therefore, performance variations of the optical system and secular changes in the optical system can be flexibly dealt with, and it is made possible to reduce the cost.

In the biochip reader, the plurality of microlenses are formed by distributing areas having a refractive index different from a refractive index of a substrate of the microlens plate on the substrate. Therefore, performance variations of the optical system and secular changes in the optical system can be flexibly dealt with, and it is made possible to reduce the cost.

In the biochip reader, the microlens plate is glass or resin. Therefore, performance variations of the optical system and secular changes in the optical system can be flexibly dealt with, and it is made possible to reduce the cost.

In the biochip reader, the driving section rotates the microlens plate. Therefore, performance variations of the optical system and secular changes in the optical system can be flexibly dealt with, and it is made possible to reduce the cost.

In the biochip reader, the driving section moves the microlens plate in a one-dimensional direction, a two-dimensional direction, or a three-dimensional direction. Therefore, performance variations of the optical system and secular changes in the optical system can be flexibly dealt with, and it is made possible to reduce the cost.

In the biochip reader, the driving section vibrates the microlens plate. Therefore, performance variations of the optical system and secular changes in the optical system can be flexibly dealt with, and it is made possible to reduce the cost.

In the biochip reader, each of the plurality of microlenses is circular in shape. Therefore, performance variations of the optical system and secular changes in the optical system can be flexibly dealt with, and it is made possible to reduce the cost.

In the biochip reader, the plurality of microlenses are shaped like a network. Therefore, performance variations of the optical system and secular changes in the optical system can be flexibly dealt with, and it is made possible to reduce the cost.

In the biochip reader, each of the plurality of microlenses is of any desired shape. Therefore, performance variations of the optical system and secular changes in the optical system can be flexibly dealt with, and it is made possible to reduce the cost.

In the biochip reader, the outgoing angle of outgoing light of the plurality of microlenses is within ±20 degrees. Therefore, performance variations of the optical system and secular changes in the optical system can be flexibly dealt with, and it is made possible to reduce the cost.

In the biochip reader, a ratio of a diameter of the microlenses to a curvature of the microlenses is 0.1 or less. Therefore, performance variations of the optical system and secular changes in the optical system can be flexibly dealt with, and it is made possible to reduce the cost.

According to the biochip reader, as the plurality of microlens having various different sizes are provided at arbitrary positions at random, and the outgoing angle as a result of light divergence, etc., of all microlenses is limited to a narrow angle is driven, the excitation light collected by the microlens scans the surface of the biochip. Therefore, performance variations of the optical system and secular changes in the optical system can be flexibly dealt with, and it is made possible to reduce the cost.

DETAILED DESCRIPTION OF THE PREFERRED EMBODIMENTS

Figure 1:
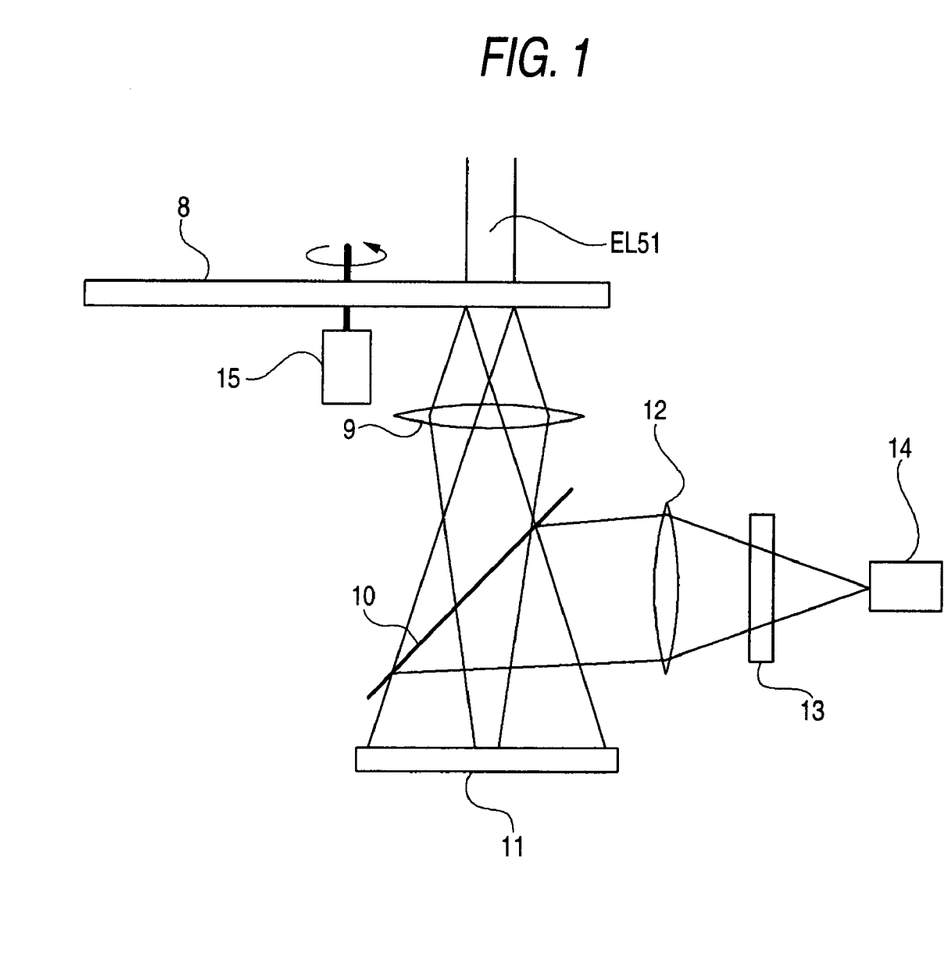
FIG. 1 is a block diagram to show the configuration of an embodiment of a biochip reader according to the invention.

The invention will be discussed in detail with the accompanying drawings. FIG. 1 is a block diagram to show the configuration of an embodiment of a biochip reader according to the invention. In FIG. 1, numeral 8 denotes a microlens plate formed with a plurality of microlenses of any desired size at any desired positions on a circular substrate, which will be hereinafter referred to as random microlens plate 8 for simplicity, numerals 9 and 12 denote lenses, numeral 10 denotes a dichroic mirror for transmitting or reflecting light in response to the wavelength of the light, numeral 11 denotes a biochip having a plurality of sites placed like an array, numeral 13 denotes a barrier filter for blocking transmission of light in a specific wavelength region, numeral 14 denotes a photographing section such as a camera, and numeral 15 denotes a driving section such as a motor for rotating the random microlens plate 8.

Excitation light indicated by "EL51" in FIG. 1, outgoing light from a light source (not shown) such as a laser light source for emitting coherent light, is applied to the random microlens plate 8, is diverged on the microlenses formed on the random microlens plate 8, and is incident on the lens 9.

The lens 9 collects the diverged excitation light and the collected excitation light is passed through the dichroic mirror 10 and is collected on the biochip 11.

Fluorescence occurring on the biochip 11 by the excitation light (specifically, fluorescence occurring on the site where a plurality of DNA pieces of the same type are placed) is reflected on the dichroic mirror 10 and the reflected light is passed through the barrier filter 13 by the lens 12 and is collected on the photographing section 14.

On the other hand, the driving section 15 rotates the random microlens plate 8 on the center axis of a disk, whereby the positions of the microlenses formed on the random microlens plate 8 move and accordingly the excitation light diverged on the microlenses and collected by the lens 9 scans over the surface of the biochip 11.

Figure 2:
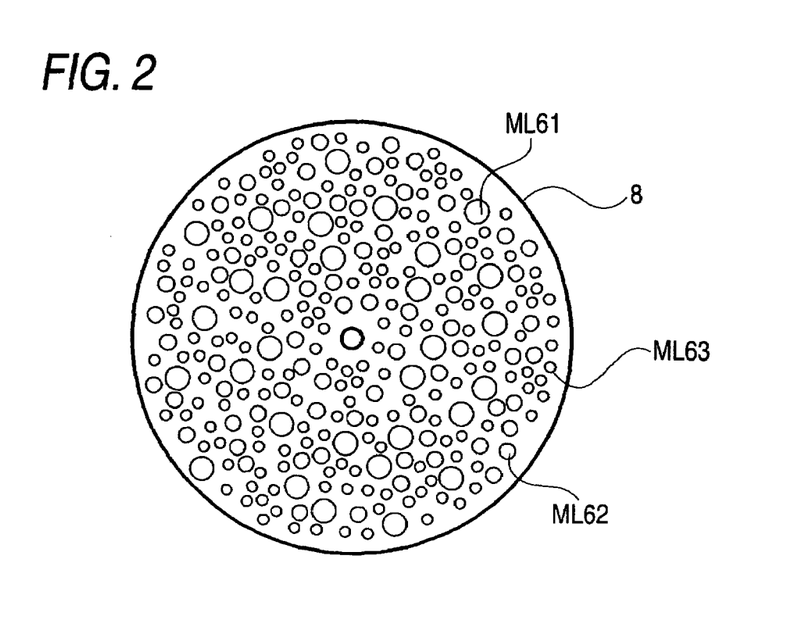
FIG. 2 is a plan view to show an example of a random microlens plate.

For example, FIG. 2 is a plan view to show an example of the random microlens plate 8. As shown in FIG. 2, the random microlens plate 8 is formed with circular microlenses of three sizes of large, medium, and small as indicated by "ML61," "ML62," and "ML63" in FIG. 2 at random at any desired positions.

The microlenses are spaced from each other for convenience of the drawing in FIG. 2; in fact, however, the microlenses are placed in a contact state with each other.

However, for all of the circular microlenses of three sizes of large, medium, and small as indicated by "ML61," "ML62," and "ML63" in FIG. 2, formed on the random microlens plate 8, the outgoing angle as a result of divergence is limited to a narrow angle to secure the amount of light incident on the light collecting lens 9.

Figure 3:
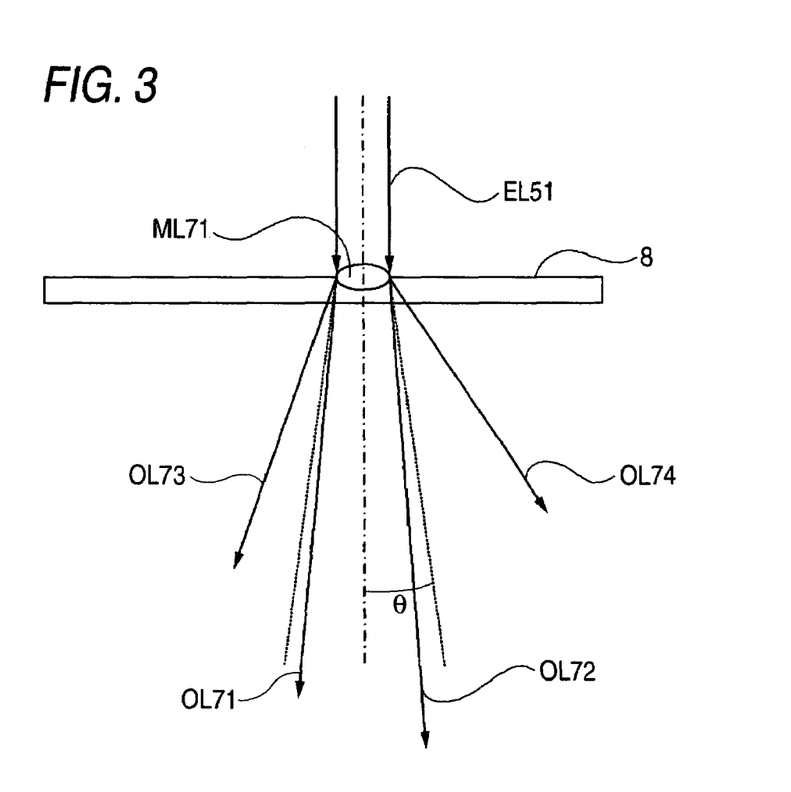
FIG. 3 is a schematic representation to describe the limitation of the outgoing angle of microlenses.

For example, FIG. 3 is a schematic representation to describe the limitation of the outgoing angle of the microlenses. Excitation light applied to the random microlens plate 8 as indicated by "EL51" in FIG. 3 is formed so as to be limited to the outgoing angle indicated by θ in FIG. 3.

Thus, outgoing light with an outgoing angle as indicated by "OL71" or "OL72" in FIG. 3 is incident on the light collecting lens 9 and light with an outgoing angle as indicated by "OL73" or "OL74" in FIG. 3 is not emitted.

Figure 4:
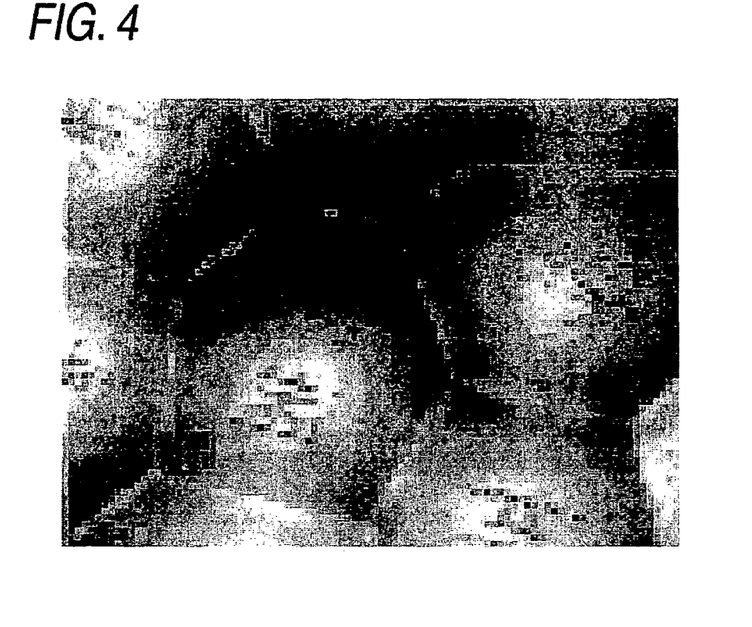
FIG. 4 is a two-dimensional image to show an example of the actual random microlens plate.
Figure 5:
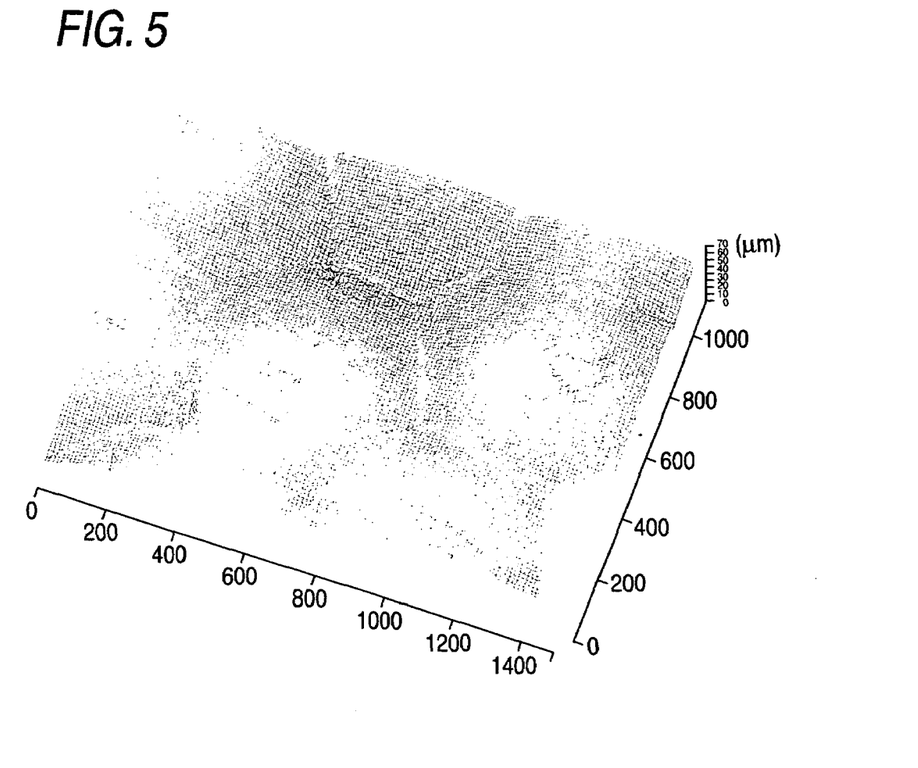
FIG. 5 is a three-dimensional image to show an example of the actual random microlens plate.
Figure 6:
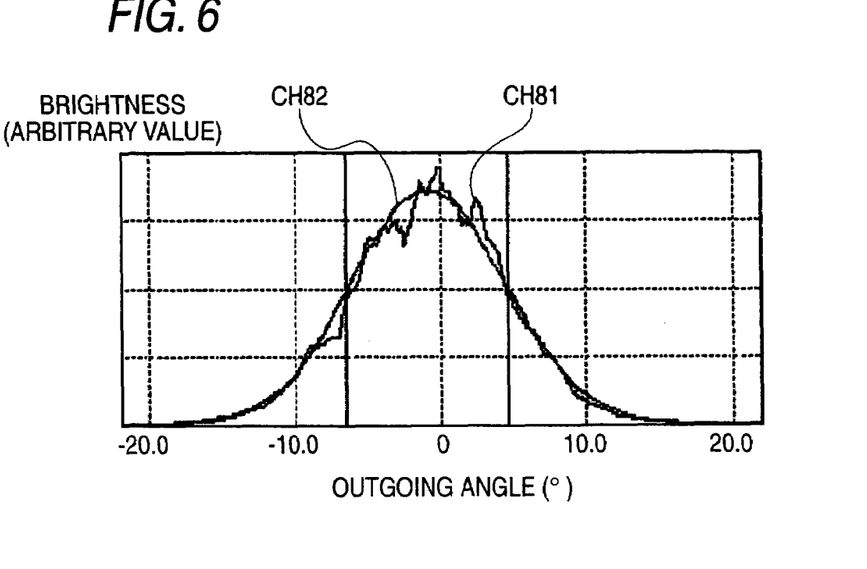
FIG. 6 is a characteristic curve drawing to show the distribution characteristic of measured outgoing angles of the random microlens plate.

FIGS. 4 and 5 are a two-dimensional image and a three-dimensional image to show an example of the actual random microlens plate 8. FIG. 6 is a characteristic curve drawing to show an example of the distribution characteristic of outgoing angles measured as collimated laser light is incident on one of the such random microlens plate.

For example, the distribution characteristic of outgoing angles measured as indicated by "CH81" in FIG. 6 becomes the distribution characteristic of outgoing angles measured as indicated by "CH82" in FIG. 6 by regression analysis. From the characteristic curve indicated by "CH82" in FIG. 6, it is seen that the angle is 10 degrees as "1/$e^2$" and the outgoing angle is limited to a narrow angle.

Figure 7:
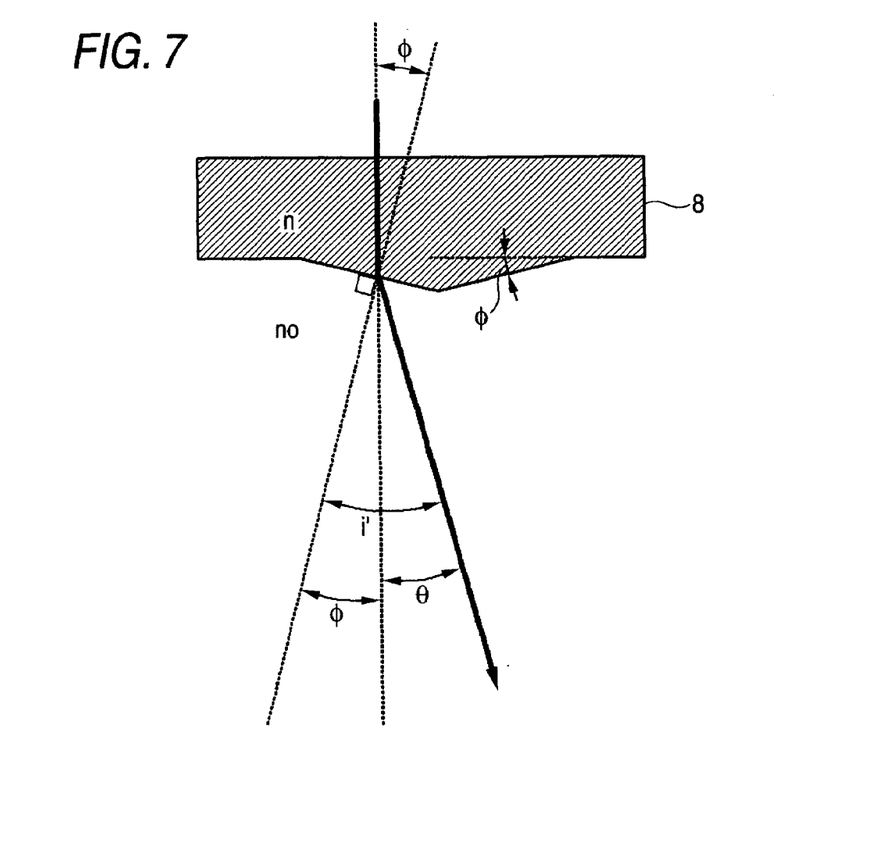
FIG. 7 is a schematic drawing to describe an outgoing angle limiting method when each formed microlens is shaped like a cone.
Figure 8:
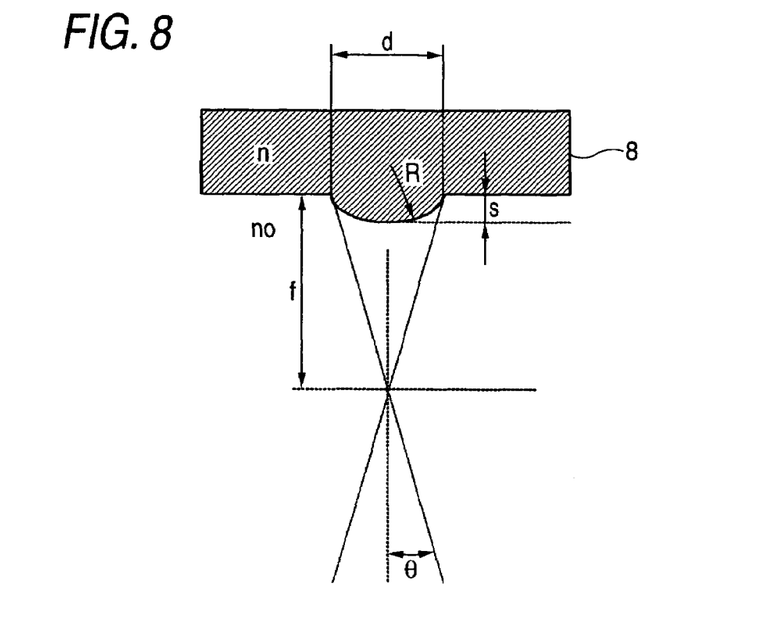
FIG. 8 is a schematic drawing to describe an outgoing angle limiting method when each formed microlens is a convex sphere.
Figure 9:
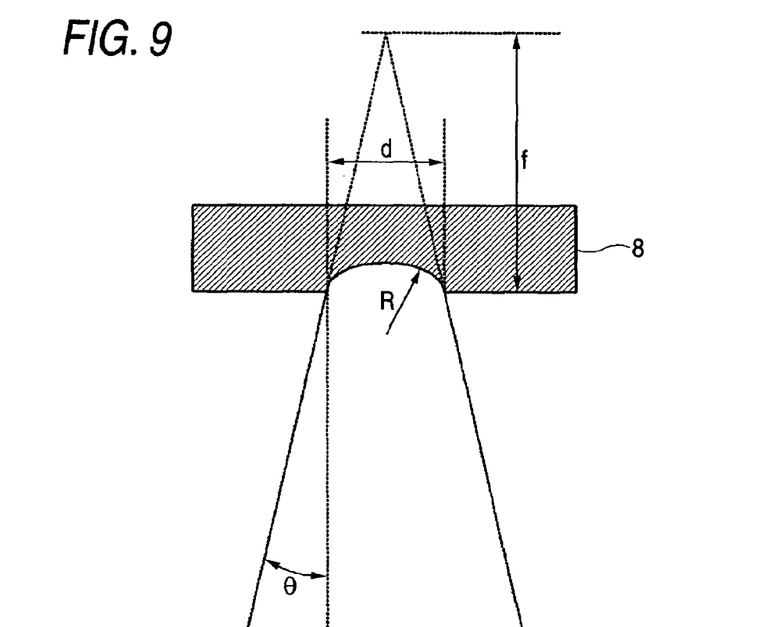
FIG. 9 is a schematic drawing to describe an outgoing angle limiting method when each formed microlens is a concave sphere.

Further, a specific method of limiting the outgoing angle will be discussed in detail with FIGS. 7, 8, and 9. FIG. 7 is a schematic drawing to describe the outgoing angle limiting method when each formed microlens is shaped like a cone. FIG. 8 is a schematic drawing to describe the outgoing angle limiting method when each formed microlens is a convex sphere. FIG. 9 is a schematic drawing to describe the outgoing angle limiting method when each formed microlens is a concave sphere.

When the microlens is shaped like a cone, in FIG. 7, letting the outgoing angle from the microlens be "θ", the inclination angle of the cone-shaped microlens be "φ", the refractive index of air be "$n_o$", and the refractive index of the random microlens plate 8 be "n", from Snell laws of refraction, $$i' = \phi + \theta$$

$$\sin i' = (n/n_o) \sin \phi$$

$$\therefore \phi = \sin^{-1}((n_o/n) \times \sin i')$$

For example, setting i'=15°, n=1.5, and no=1.0 and setting the inclination angle of the cone-shaped microlens, φ, as $$\phi = \sin^{-1}((1/1.5)) \times \sin 15°)$$

$$\approx 9.9°$$

Thus, θ=i'−φ=5.0°

The outgoing angle "θ" can be limited to a narrow angle.

On the other hand, when the microlens is a convex or concave sphere, in FIGS. 8 and 9, letting the outgoing angle from the microlens be "θ", the diameter of the spherical microlens be "d", the focal distance of the spherical microlens be "f", the curvature radius of the spherical microlens be "R", the numerical aperture of the spherical microlens be "NA", the refractive index of air be "no", and the refractive index of the random microlens plate 8 be "n,"

$$f = R/(n-no)$$

$$NA \approx f/(d/2 = 2R/(d \times (n-no))$$

Here, for example, setting n=1.5 and no=1.0, $$NA \approx 4R/d$$

$$R/d \approx NA/4$$

Thus, "R/d" is limited, whereby the outgoing angle "θ" can be limited to a narrow angle.

Letting the sag (lug amount) of the spherical microlens be "S,"

$$S = R - (R^2 - (d/2)^2)^{1/2}$$

Further, letting average inclination angle "φ'" be "S/(d/2),"

$$\phi' = S/(d/2)$$
$$= R/(d/2) - (R/(d/2)^2 - 1)^{1/2}$$

"R/d" is limited, whereby the average inclination angle "φ'" can be determined uniquely.

For example, if "NA" is within about 0.4 (θ26 24 degrees), the light collecting lens 9 is easily available. In this case, $$R/d \approx NA/4 = 0.1$$

Thus, as the random microlens plate 8 formed with the circular microlens of different sizes at random at any desired positions where the outgoing angle as a result of light divergence of all microlens is limited to a narrow angle is rotated, excitation light collected on the microlens scans over the surface of the biochip 11, whereby the illumination is smoothed and an image with an even light amount is provided.

Figure 10:
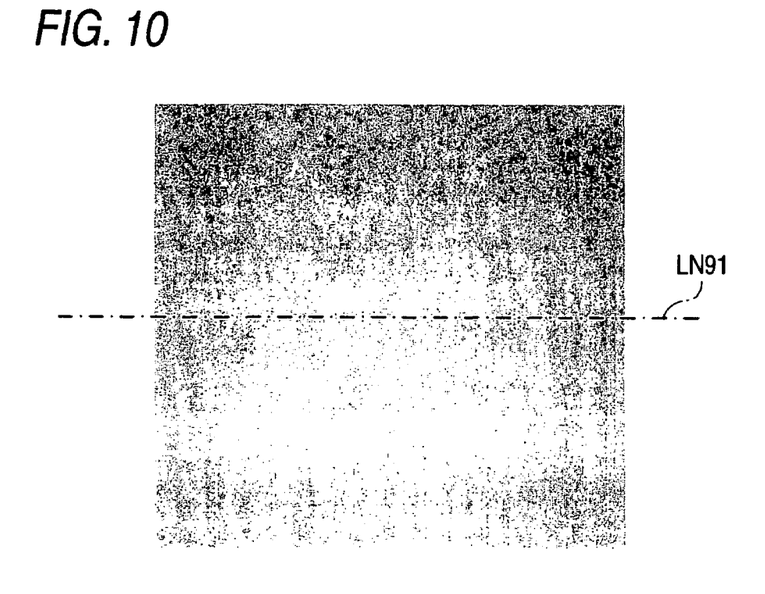
FIG. 10 is a schematic representation to show an example of a photograph image when the random microlens plate is rotated and a fluorescent plate for uniformly producing fluorescence in response to excitation light is used instead of a biochip.
Figure 11:
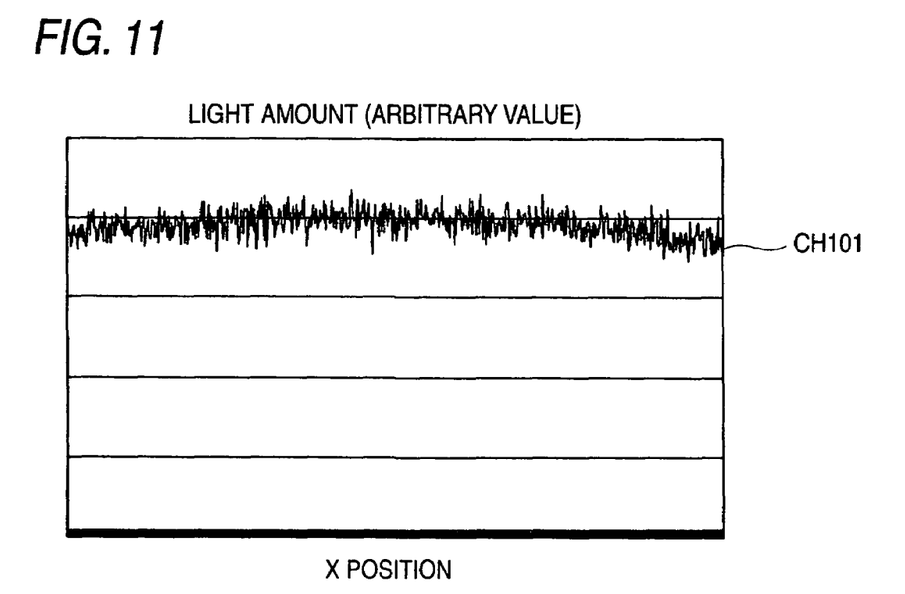
FIG. 11 is a schematic representation to show an example of the distribution characteristic of any axial light amounts when the random microlens plate is rotated and a fluorescent plate for uniformly producing fluorescence in response to excitation light is used instead of a biochip.

For example, FIGS. 10 and 11 are schematic representations to show examples of a photograph image and the distribution characteristic of any axial light amounts when the random microlens plate 8 is rotated and a fluorescent plate for uniformly producing fluorescence in response to excitation light is used instead of the biochip 11.

As shown in FIG. 10, it is seen that the photograph image becomes an image with uniform light amount and patterns like unevenness and interference fringes caused by performance variations such as light distribution unevenness of the outgoing light of the laser light source or dirt and secular changes in the optical system are not reflected on the photograph image unlike the image shown in FIG. 20 in the related art example.

It is also seen that the characteristic curve of light amounts is uniform and performance variations such as light distribution unevenness of the light source or dirt and secular changes in the optical system are flexibly dealt with in "CH101" in FIG. 11 indicating the light quantity distribution on the line indicated by "LN91" in FIG. 10.

Further, to rotate the random microlens plate 8 formed with the circular microlens of different sizes at random at any desired positions where the outgoing angle as a result of light divergence of all microlens is limited to a narrow angle, accurate registration of the formation positions of the microlenses and rotation synchronization become unnecessary, so that the cost can be reduced.

Consequently, as the random microlens plate 8 formed with the microlens of different sizes at random at any desired positions where the outgoing angle as a result of light divergence of all microlens is limited to a narrow angle is rotated, excitation light collected by the microlens scans over the surface of the biochip 11, whereby performance variations of the optical system and secular changes in the optical system can be flexibly dealt with, and it is made possible to reduce the cost.

If non-coherent light is used for white light to measure a biochip, noise as with a laser is hard to occur, but background noise as shown below worsens. In the embodiment shown in FIG. 1, the barrier filter 13 is placed preceding the photographing section 14. For example, FIGS. 12 and 13 are schematic representations to describe the amount of light received at the photographing section 14 if the light source is a white light source and a laser light source.

Figure 12:
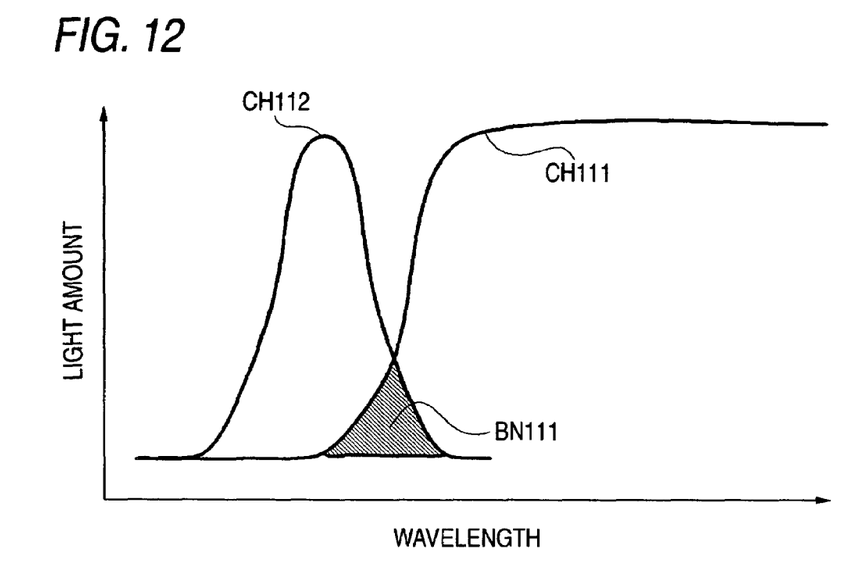
FIG. 12 is a schematic representation to describe the amount of light received at a photographing section if the light source is a white light source.

If the transmission characteristic of the barrier filter 13 is a characteristic indicated by "CH111" in FIG. 12 and white light is applied to a biochip as excitation light, the excitation light has a wavelength distribution with a spread base as indicated by "CH112" in FIG. 12 and thus the portion indicated by "BN111" in FIG. 12 cannot sufficiently be shielded and background noise occurs.

Figure 13:
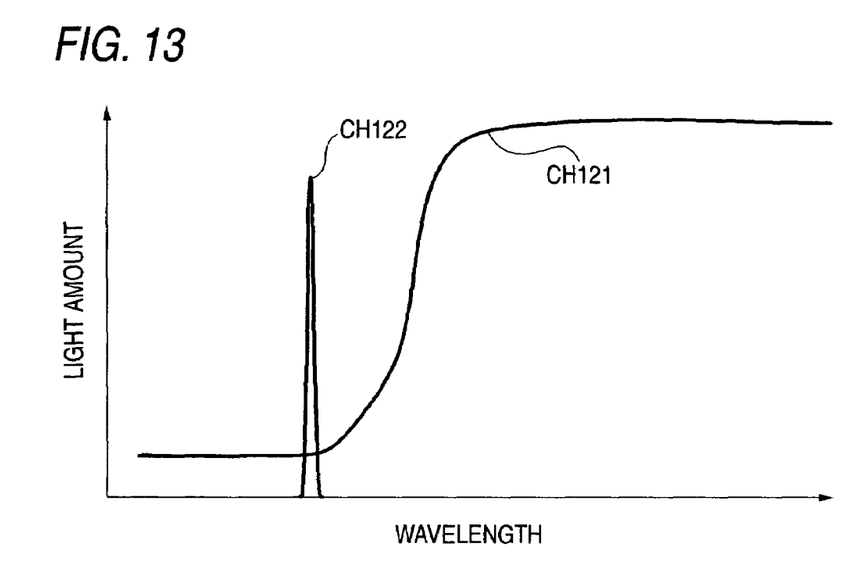
FIG. 13 is a schematic representation to describe the amount of light received at photographing section if the light source is a laser light source.

In contrast, if the transmission characteristic of the barrier filter 13 is a characteristic indicated by "CH121" in FIG. 13 and laser light is applied to a biochip as excitation light, the excitation light has a wavelength distribution with an extremely narrow base as indicated by "CH122" in FIG. 13 and thus the barrier filter 13 can sufficiently shield the portion indicated by "BN111" in FIG. 12 and it is made possible to reduce background noise.

In the embodiment shown in FIG. 1, the dichroic mirror allows excitation light to pass through and reflects fluorescence occurring on a biochip; of course, the dichroic mirror may reflect excitation light and may allow fluorescence occurring on a biochip to pass through.

In the embodiment shown in FIG. 1, specifically, as for the shape of each microlens formed on the random microlens plate 8 shown in FIG. 2, the circular microlens is shown by way of example for simplicity of the description; of course, the shape of each microlens is not limited to the circular shape.

Figure 14:
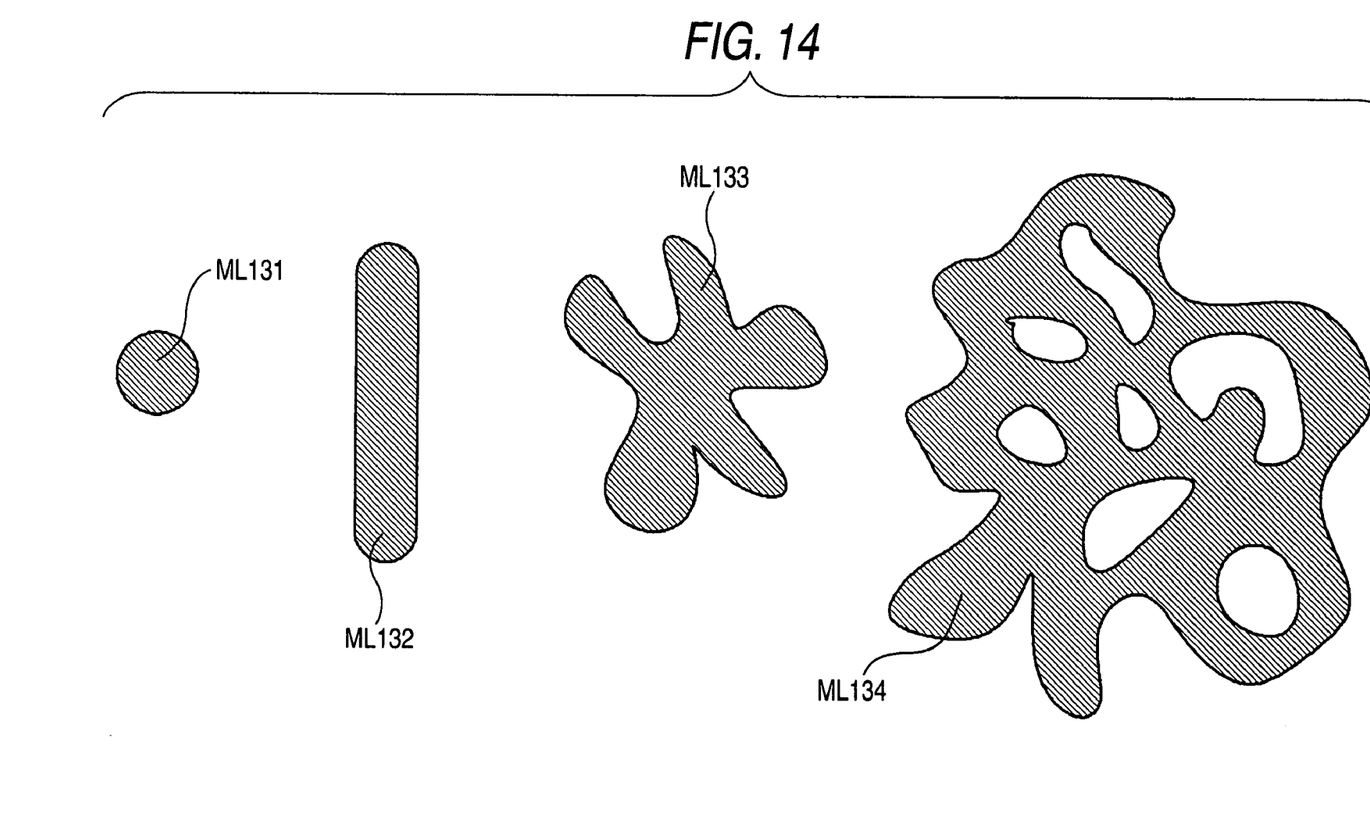
FIG. 14 is a schematic representation to show other examples of the shape of each microlens formed on the random microlens plate.
Figure 15:
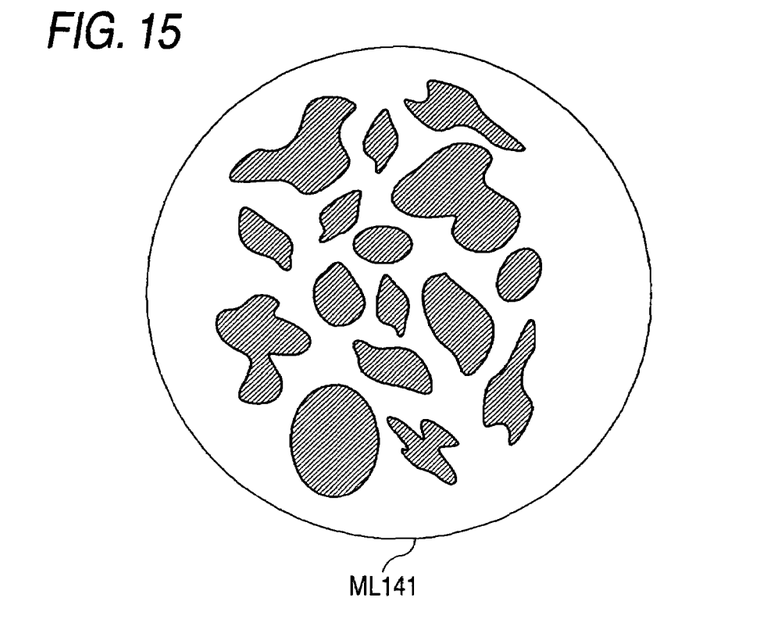
FIG. 15 is a schematic representation to show another example of the shape of each microlens formed on the random microlens plate.

FIGS. 14 and 15 are schematic representations to show other examples of the shape of each microlens formed on the random microlens plate 8. The shape of each microlens may be not only a circular shape as indicated by "ML131" in FIG. 14, but also a cylindrical shape as indicated by "ML132" in FIG. 14, a polygonal shape, a closed free curve shape as indicated by "ML133" in FIG. 14, a network shape as indicated by "ML134" in FIG. 14, etc. In other words, any desired shape may be adopted.

Further, the microlens may adopt a shape like an arrangement of a large number of islands as indicated by "ML141" in FIG. 15. However, if any shape is adopted, there is the necessity for limiting the outgoing angle as a result of light divergence of all microlens to a narrow angle. The microlens may be not only spherical in shape, but also like a prism or a ramp in shape.

Glass, resin, etc., can be used as the material of the random microlens plate 8 formed with the circular microlens of different sizes at random at any desired positions where the outgoing angle as a result of light divergence of all microlens is limited to a narrow angle.

The excitation light incident on the random microlens plate 8 may be not only collimated light, but also convergent light or divergent light if the range is a range in which the outgoing angle of outgoing light is limited to a narrow angle.

In the embodiment shown in FIG. 1, etc., projections and depressions are formed on the random microlens plate 8 (substrate) to form the microlenses, but an area having a different refractive index from the essential refractive index of the random microlens plate 8 (substrate) may be distributed on the random microlens plate 8 (substrate) to form the microlenses.

In this case, the shape of the area having a different refractive index from the essential refractive index of the random microlens plate 8 (substrate) is not limited to a circular shape, and any desired shape as shown in FIGS. 14 and 15 can be used.

The distance between the focal position of the light collecting lens 9 and the biochip 11 may be shifted, in other words, the proper focus may be shifted, thereby improving the randomization effect of the random microlens plate 8.

In the embodiment shown in FIG. 1, as the random microlens plate 8 is rotated, excitation light collected by the microlens scans over the surface of the biochip 11, but the drive method is not limited to rotation. Light may scan over the surface of the biochip 11 as the random microlens plate 8 is moved like a parallel move, etc., on the plane parallel with the biochip 11.

Further, the random microlens plate 8 may be moved not only on the plane, but also in any desired direction because alignment between the random microlens plate 8 and the biochip 11 is not strict. The random microlens plate 8 may be vibrated.

In the embodiment shown in FIG. 1, excitation light is diverged by the microlenses formed on the random microlens plate 8, but light provided by once collecting the excitation light may be used.

Figure 16:
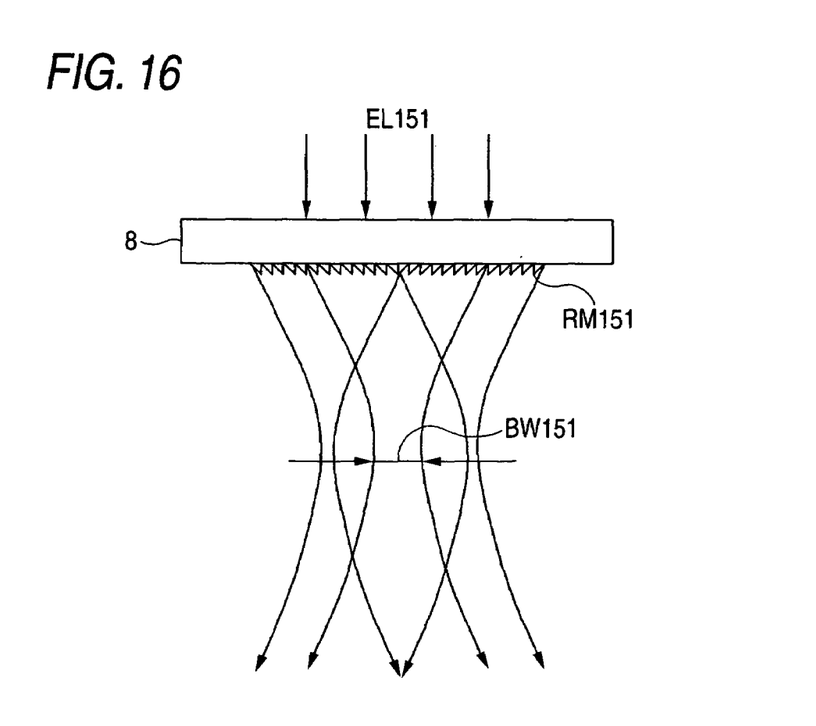
FIG. 16 is a schematic representation to show the case where light provided by once collecting excitation light is used.

FIG. 16 is a schematic representation to show the case where light provided by once collecting excitation light is used. The random microlens plate 8 may be formed with a large number of ramp-shaped projections as indicated by "RM151" in FIG. 16, and excitation light after excitation light indicated by "EL151" in FIG. 16 is collected and a beam waist as indicated by "BW151" in FIG. 16 is formed may be applied to a biochip. In this case, the light collecting lens 9 becomes unnecessary.

What is claimed is:

1. A biochip reader, comprising:
    a microlens plate on which a plurality of microlenses, whose outgoing angle of divergence light or collection light is limited to a narrow angle, are provided at arbitrary positions, wherein each of the plurality of the microlenses has arbitrary size;
    a light source which applies coherent light to the microlens plate as excitation light;
    a dichroic mirror which transmits or reflects outgoing light from the microlens plate, and reflects or transmits fluorescence occurring on a biochip;
    a photographing section;
    a lens which collects the light reflected or transmitted on the dichroic mirror into the photographing section;
    a barrier filter provided between the dichroic mirror and the photographing section; and
    a driving section which drives the microlens plate,
    wherein while the driving section drives the microlens plate, excitation light diverged or collected by the plurality of microlenses scans a surface of the biochip.

2. The biochip reader according to claim 1,
wherein the plurality of microlenses are formed by providing projections and depressions on a substrate of the microlens plate.

3. The biochip reader according to claim 1,
wherein the plurality of microlenses are formed by distributing areas having a refractive index different from a refractive index of a substrate of the microlens plate on the substrate.

4. The biochip reader according to claim 1,
wherein the microlens plate is glass or resin.

5. The biochip reader according to claim 1,
wherein the driving section rotates the microlens plate.

6. The biochip reader according to claim 1,
wherein the driving section moves the microlens plate in a one-dimensional direction, a two-dimensional direction, or a three-dimensional direction.

7. The biochip reader according to claim 1,
wherein the driving section vibrates the microlens plate.

8. The biochip reader according to claim 1,
wherein each of the plurality of microlenses is circular in shape.

9. The biochip reader according to claim 1,
wherein the plurality of microlenses are shaped like a network.

10. The biochip reader according to claim 1,
wherein each of the plurality of microlenses is of any desired shape.

11. The biochip reader according to claim 1,
wherein the outgoing angle of outgoing light of the plurality of microlenses is within ±20 degrees.

12. The biochip reader according to claim 8,
wherein a ratio of a diameter of the microlenses to a curvature of the microlenses is 0.1 or less.

* * * * *